(12) United States Patent
Horch et al.

(10) Patent No.: US 10,675,383 B2
(45) Date of Patent: Jun. 9, 2020

(54) SILICONE BREAST IMPLANT WITH REINFORCING FIBERS

(71) Applicant: Friedrich-Alexander-Universitat Erlangen-Nurnberg, Erlangen (DE)

(72) Inventors: Raymund Horch, Erlangen (DE); Dirk W. Schubert, Eggolsheim (DE); Siegfried Werner, Erlangen (DE); Mikael Hedenqvist, Saltsjobaden (SE); Richard Tobias Olsson, Lidingo (SE)

(73) Assignee: Freidrich-Alexander-Universität Erlangen-Nürnberg, Erlangen (DE)

( * ) Notice: Subject to any disclaimer, the term of this patent is extended or adjusted under 35 U.S.C. 154(b) by 134 days.

(21) Appl. No.: 15/779,577

(22) PCT Filed: Nov. 28, 2016

(86) PCT No.: PCT/EP2016/078990
§ 371 (c)(1),
(2) Date: May 29, 2018

(87) PCT Pub. No.: WO2017/093181
PCT Pub. Date: Jun. 8, 2017

(65) Prior Publication Data
US 2019/0262506 A1  Aug. 29, 2019

(30) Foreign Application Priority Data

Nov. 30, 2015  (EP) ................................. 15197017

(51) Int. Cl.
| | |
|---|---|
| *A61L 27/48* | (2006.01) |
| *C08G 81/02* | (2006.01) |
| *C08J 5/04* | (2006.01) |
| *B05D 1/18* | (2006.01) |
| *D01D 5/00* | (2006.01) |
| *D01F 6/36* | (2006.01) |
| *A61L 27/34* | (2006.01) |

(52) U.S. Cl.
CPC ............... *A61L 27/48* (2013.01); *A61L 27/34* (2013.01); *B05D 1/18* (2013.01); *C08G 81/024* (2013.01); *C08J 5/046* (2013.01); *D01D 5/003* (2013.01); *D01F 6/36* (2013.01); *A61L 2430/04* (2013.01)

(58) Field of Classification Search
CPC ............ A61L 27/48; A61L 27/34; C08J 5/046
See application file for complete search history.

(56) References Cited

U.S. PATENT DOCUMENTS 5,053,048 A * 10/1991 Pinchuk .............. A61L 33/0029
128/DIG. 21
5,376,117 A  12/1994 Pinchuk

OTHER PUBLICATIONS

Bayley et al., "Large strain and toughness enhancement of poly(dimethyl siloxane) composite films filled with electrospun polyacrylonitrile-graft-poly(dimethyl siloxane) fibres and multi-walled carbon nanotubes," Polymer, vol. 52, pp. 4061-4072 (2011).
Daniels, "Silicone breast implant materials," Swiss Med Wkly. 2012;142:w13614.
Schubert et al., "On the failure of silicone breast implants: new insights by mapping the mechanical properties of implant shells," Polym Int, Wiley Online Library, DOI 10.1002/pi.4619 (2013).
Swart et al., "Organic-Inorganic Hybrid Copolymer Fibers and Their Use in Silicone Laminate Composites," Polymer Engineering and Science, DOI 10.1002/pen.21749 (2010).
International Search Report for PCT/EP2016/078990, dated Feb. 20, 2017.
International Preliminary Report on Patentability for PCT/EP2016/078990, dated Jun. 5, 2018.

* cited by examiner

Primary Examiner — Jeffrey C Mullis
(74) Attorney, Agent, or Firm — Sonapat LLC (57) ABSTRACT

Subject of the invention is a medical implant comprising a fiber reinforced silicone comprising (A) a silicone matrix and (B) fibers embedded in the silicone matrix, wherein the fibers comprise a comb polymer having a base polymer and side chains, wherein the base polymer is an organic polymer and the side chains comprise polysiloxanes. The invention also relates to outer shells of breast implants and uses and methods.

20 Claims, 4 Drawing Sheets

SILICONE BREAST IMPLANT WITH REINFORCING FIBERS

The invention relates to a medical implant comprising a fiber reinforced silicone comprising a silicone matrix and fibers embedded in the silicone matrix. The invention also relates to outer shells of breast implants, uses and methods.

STATE OF THE ART

Silicone implants are used in surgery because of various advantageous properties, especially good biocompatibility, elasticity and long-term stability. An important application is the use as breast implants. Silicone breast implants have been developed and used since the 1970s and it is estimated that worldwide more than 15 million women are carrying such breast implants. Subsequently, improved materials have been developed with enhanced stability and compatibility with the surrounding tissue. Silicone breast implants are implanted under the breast tissue or under the chest muscle for breast augmentation or for the purpose of breast reconstruction, for example following breast cancer or benign breast diseases. Breast implants possess an outer shell based on crosslinked silicone that is normally filled with a silicone gel consisting of a weakly crosslinked silicone and uncrosslinked silicone. Breast implants are available in many different sizes and have either smooth or textured shells. Materials for silicone breast implants and their properties are described in Daniels, 2012, Colas, 2005, and Daenicke, 2012.

Since such silicone breast implants have been used, it has been a problem to determine and optimize the materials with respect to stability, biocompatibility and safety. The implant has to remain stable and functional for a long time over years or even decades. Since the findings of the French health authorities regarding deficiencies of silicone gel-filled breast implants manufactured by Poly Implant Prothese (PIP), silicone breast implants have hit the headlines and attracted scientific interest. It became clear that damages of such implants with time, especially rupture and cracks, are a tremendous practical problem. It was found that long-time in vivo stability of the implants could not simply be correlated to mechanical stability determined theoretically. It is difficult to provide implants having long term stability, which at the same time have a good biocompatibility and elasticity in the human body. Moreover, it is difficult to monitor and evaluate such materials which are not accessible in vivo. Overall, the mechanisms for adjusting long-term stability and avoiding damages with time were not sufficiently understood. Daniels, 2012, provides an overview on silicone breast implant materials and their properties and discusses problems regarding stability, safety and biocompatibility.

Schubert et al., 2013, proposed novel mappings for silicone breast implants for assessing their stability. The method illustrates local variations within one implant revealing the manufacturers potentials to optimize the production processes with respect to resilience and related homogeneity. The method utilizes Weibull statistics and the characteristic parameters $\sigma_0$ and m as a coordinate system for demonstrating how implants can be analysed, benchmarked and clustered. As a result, it was found that many silicone materials commonly used in the art do not have optimal stability for long-term applications. A detailed analysis is also provided in Daenicke, 2012.

U.S. Pat. No. 5,376,117 discloses breast implants in which a silicone matrix is reinforced with polyurethane fibers. However, the compatibility of polyurethane with polysiloxanes is generally not adequate. The compatibility of the components of such composite materials is highly important after implantation, because even minor segregation of the components will result in severe problems after years or decades and ultimately, the overall structure can be ruptured or collapse. To the knowledge of the applicant, materials as described in U.S. Pat. No. 5,376,117 have not been certified or practically put into use.

In general, there is a need in the art for improved implants, which overcome the above mentioned problems. Specifically, there is a need for breast implants having improved long-term stability, but also an appropriate biocompatibility and safety.

Problem Underlying the Invention

The problem underlying the invention is to provide breast implants which overcome the above-described problems. An implant shall be provided which has improved stability. Especially, the long-term stability shall be advantageous. The susceptibility to damage, especially rupture and cracks, shall be low. Further, the biocompatibility and safety shall be adequate. Advantageous methods shall be provided for producing such breast implants and materials.

DISCLOSURE OF THE INVENTION

Surprisingly, it was found that the problem underlying the invention is overcome by implants, outer shells, methods and uses according to the claims. Further embodiments of the invention are outlined throughout the description.

Subject of the invention is an outer shell for a breast implant, wherein the outer shell comprises a fiber reinforced silicone comprising
(A) a silicone matrix and
(B) fibers embedded in the silicone matrix,
wherein the fibers comprise a comb polymer having a base polymer and side chains, wherein the base polymer is an organic polymer and the side chains comprise polysiloxanes.

The outer shell is for a breast implant. In a preferred embodiment, the implant comprises an outer shell and a core, wherein the outer shell comprises the fiber reinforced silicone. Preferably, the outer shell consists of the fiber reinforced silicone.

The breast implant is for application to female humans. The shape of a breast implant is adapted to the shape of a female breast, and normally corresponds to the shape of the breast. Further, a breast implant is at least in part elastomeric and the elasticity is adapted to the female breast. Typically, a breast implant comprises an outer shell of a crosslinked silicone and a core filled with a silicone which is not crosslinked and/or weakly crosslinked. Alternatively, the outer shell is filled with a saline solution. Silicone breast implants and materials for their production are disclosed, for example, in Daniels, 2012.

The fiber reinforced silicone is elastomeric. It comprises a silicone matrix (A) with fibers embedded therein. Silicones are mixed inorganic-organic polymers comprising repetitive units of chemical formula $(R_2SiO)_n$, wherein R is an organic side group (typically methyl). Thus, silicone comprise a backbone of alternating Si—O units, to which the organic side groups are attached. Such polymers are also referred to as polysiloxanes. The most common polysiloxane is poly-dimethylsiloxane (PDMS). Typically, polysiloxane and PDMS chains are terminated with alkyl groups, for example alkyl groups having 1 to 10 carbon atoms, especially 1 to 5 carbon atoms, often methyl. Typically, the polysiloxane or PDMS is trimethylsilyl terminated. PDMS is a viscous liquid, the viscosity of which increases with the chain length.

The silicone matrix (A) forms a three dimensional network. A silicone matrix is formed by crosslinking silicone polymers. Preferably, the silicone matrix is at least partially crosslinked. Thus, the polysiloxane chains comprise crosslinking sites, which link different chains with each other. Crosslinked silicones are known and used in the art as the standard structural material for breast implants. Crosslinking groups may be vinyl, hydroxyl, acetyl, acyl, alkoxyl, —H or halogen. Crosslinking sites are often vinyl groups which can be crosslinked with radicals or by addition in the presence of catalysts. Alternatively, the silicone may comprise acetoxy and/or hydroxyl groups and can be crosslinked by condensation. The number of crosslinking sites determines the strength of the three-dimensional matrix. Silicone polymers for breast implants and methods for producing them are described in Daniels, 2012, and Colas, 2005. Preferably, the silicone matrix is at least partially crosslinked PDMS.

Silicones for producing crosslinked silicones are commercially available, typically in the form of two precursor components, which are a liquid silicone component (silicone rubber) and a separate crosslinking agent. The liquid silicone component is mixed with the crosslinking agent in a desired three-dimensional form in a mould and the solution is cured. A liquid silicone rubber for preparing elastomeric silicone is available under the trademark ELASTOSIL LR 3003/30 from Wacker, DE. A solvent-free silicone for addition-curing is available under the trademark DEHESIVE 920 from Wacker, DE.

The silicone matrix comprises fibers embedded in the silicone matrix. In this respect, the term "embedded" means that the fibers, or at least the vast majority or fibers, are covered with silicone, for example such that at least 95%, at least 98% or 100% of the overall fiber surface is covered.

The fibers comprise a comb polymer having a base polymer and side chains. The term "comb polymer" reflects that the chemical structure of a polymer resembles a comb, whereby the side chains are the comb teeth.

Preferably, the base polymer is an organic polymer. This means that the base polymer is carbon-based and does not comprise Si, for example in the form of silicone or polysiloxane units. Typically, the base polymer consists of the elements C, H and optionally N and/or O. In another embodiment, the base polymer may comprise Si, for example in the form of silicone or polysiloxane units.

The side chains comprise polysiloxanes. As outline above, a polysiloxane comprises repetitive units of the chemical formula $(R_2SiO)_n$, wherein R is an organic residue, typically alkyl having 1 to 5 carbon atoms, preferably methyl. Typically, the number of units n in a side chain is between 5 and 1,000, preferably between 20 and 250. Typically, a side chain is a polysiloxane unit, which is terminated with an alkyl group, preferably having 1 to 18 carbon atoms, more preferably 2 to 6 carbon atoms. In a specific embodiment, it is terminated with a trimethylsilyl group.

In a preferred embodiment, the polysiloxane side chains are linked to the base polymer by ester, amide or ether bonds or by an alkylene group —$(CH_2)_x$— wherein x is between 1 to 6. Preferably, the polysiloxane side chains are linked to the base polymer by ester bonds.

In a preferred embodiment, the comb polymer comprises
a) at least one structural unit A wherein $R^1$ independently of one another represents —H or —$CH_3$;

$R^2$ independently of one another represents an ester group —CO—O—, an amide group —CO—NH—, an ether group —O— or no group,

$R^3$ independently of one another represents —$R^7$—Y—, wherein $R^7$ is a $C_1$-$C_6$ alkylene group, especially a methylene, ethylene or propylene group, and Y is either no atom or O, $R^4$ independently of one another represents $C_1$-$C_4$ alkyl, preferably methyl or ethyl, $R^5$ independently of one another represents $C_1$-$C_{18}$ alkyl, preferably $C_1$-$C_6$ alkyl, n independently of one another is a value between 5 and 2000, preferably between 20 and 1000, most preferably between 30 and 500, and b) at least one structural unit B wherein $R^1$ independently of one another represents H or $CH_3$;

$R^2$ independently of one another represents H or $CH_3$, preferably H, $R^3$ independently of one another represents H or $CH_3$, preferably H, $R^4$ independently of one another represents H, —CN, —COO—$R^6$, —O—$R^6$, —CO—N—$R^6$ or —$R^6$, wherein $R^6$ is $C_1$-$C_8$ alkyl, preferably methyl or ethyl.

In a preferred embodiment, structural unit A is defined as follows: $R^1$ is $CH_3$, $R^2$ is —CO—O—, $R^3$ is a $C_1$-$C_6$ alkylene group, $R^4$ is methyl, n is between 20 and 1,000, $R^5$ is $C_1$-$C_6$ alkyl. In a preferred embodiment, structural unit B is defined as follows: $R^1$ is $CH_3$, $R^2$ is H, $R^3$ is H and $R^4$ is selected from —CN and —COO—$R^6$, wherein $R^6$ is $C_1$-$C_2$ alkyl.

In preferred embodiments, the comb polymer has a chemical structure of formula (I) or (II) as shown below.

Formula (I)

Formula (II)

The comb polymer of formula (II) is especially preferred, because the chemical structure is especially suitable for use in an implant. Polymers of formula (II) are poly(methyl methacrylate)-graft-poly(dimethyl siloxane) copolymers (PMMA-g-PDMS). They can be prepared according to Swart et al., 2010. Polymers of formula (I) can be prepared according to Bayley et al., 2011.

Preferably, the comb polymer is a copolymer. The comb polymer may be a graft copolymer. Preferably, the polymer is a random copolymer, in which subunits A and B are randomly distributed along the polymer chain.

The molecular weight (or molar mass according to IUPAC terminology) of the polysiloxane side chains could be between 100 and 25,000, preferably between 200 and 10,000 g/mol.

The amount of polysiloxane in the comb polymer could be between 1 and 50%, preferably between 2 and 30%, or between 3 and 20% (w/w). Typically, subunit B is present in a significant molar excess. Thus, the molar ratio of subunit B/subunit A is significantly above 1, typically above 5 or above 10.

The comb polymer can be prepared by polymerising a polysiloxane monomeric subunit, which comprises with a terminal polymerisation site. Such an activated polymer for further polymerization is also named macromer. The polymerisation site typically comprises an activated C=C double bond, such as a methacrylate group. When the comb polymer is a copolymer, the macromere is polymerized with at least one other monomer, such as acrylonitrile or methylmethacrylate. Typically, all monomer for polymerization comprise activated C=C double bonds.

In a preferred embodiment, the fibers are spun from the comb polymer. Preferably, the fibers are spun from a solution of the comb polymer in solvent.

In a preferred embodiment, the fibers are electrospun. During electrospinning, a high voltage causes charges to be induced in a polymer solution. Above a critical point, the charges cause a fluid jet to erupt from the tip of a pipette or needle, resulting in formation of a fluid cone. The jet thus formed travels towards a grounded collector plate upon simultaneous evaporation of the solvent, which results in formation of very thin polymer fibers in the nanometer or micrometer range. Electrospinning of polymers of formula (I) or (II) above into fibers has been described in the art. In this respect, reference is made to Swart et al., 2010, and Bayley et al., 2011. It is highly preferred to use comb polymers, electrospun fibers, fiber reinforced silicone materials and electrospinning processes as described in these publications in the present invention.

In a preferred embodiment, the fibers have an average diameter of 10 nm to 50 μm, preferably between 50 nm and 10 μm, most preferably between 100 nm and 5 μm. The fibers should be sufficiently fine to provide high uniformity of the composite material. However, they should be sufficiently thick to stabilize the composite material. Typically, the average fiber diameter is determined by the median of the fiber diameter frequency distribution.

In a preferred embodiment, the fibers (B) consist of the comb polymer. However, the fibers or fiber-reinforced silicone may comprise additional components, which enhance the strength or confer other advantageous properties to the fibers or implant. For example, the fibers may comprise up to 50% (w/w) or up to 20% (w/w) additives. The fibers (B) may also comprise a mixture of comb polymers as described above.

In a specific embodiment, the fiber-reinforced silicone and/or fibers comprise carbon nanotubes. The carbon nanotubes can be combined with the comb polymer fibers, for example in a process as described by Bayley, 2011, for increasing the strength.

The amount of fibers in the reinforced silicone could be 0.1 to 20% (w/w), preferably 0.5 to 10% (w/w), or 1 to 5% (w/w), based on the total weight of the fiber reinforced silicone. Preferably, the fiber reinforced silicone comprises less than 15% (w/w), more preferably less than 10% (w/w) of the fibers. Preferably, the fiber reinforced silicone comprises more than 1% (w/w), more preferably more than 2% (w/w) of the fibers.

The breast implant comprises a core. Any known materials can be used as the core material. In a preferred embodiment, the core of the implant comprises a silicone gel and/or salt solution. When the core comprises a silicone gel, it is not crosslinked or only weakly crosslinked. In any case, the core of the implant does not comprise reinforcing fibers. This is not required, because the outer shell protects the implant and has to confer mechanical resilience to the overall implant.

Preferably, the outer shell consists of a fiber reinforced silicone as described above. The outer shell can be used for the production of a breast implant. Typically, such an outer shell has an opening through which the mould from the production process was removed. The inventive outer shell can be filled with the core material, and the opening can be closed and sealed by known methods.

In a preferred embodiment, the fiber reinforced silicone is a laminate. Preferably, the laminate comprises at least two layers, wherein at least one layer comprises fibers. Such fiber reinforced silicone can be produced by depositing fibers on the surface of the workpiece (the incomplete silicone in the production process) layer by layer. In intermediate steps, the silicone with fibers on the surface can be impregnated with additional liquid silicone, optionally followed by partial or complete crosslinking. Such a layer-wise production is advantageous, because the fibers can be mixed intimately with the silicone. Further, the local internal amount and distribution of fibers can be adapted to specific needs. For instance, the amount of fibers can be increased at internal sites which are more prone to rupture.

In a preferred embodiment, the fibers are arranged to strengthen predetermined regions of the fiber reinforced silicone. For example, the amount of fibers can be higher and/or the fibers can be oriented in specific regions of the fiber reinforced silicone. Preferably, these regions are potential regions of rupture. Ruptures in silicone breast implants often occur tangentially. Preferably, the regions are in the equatorial region of the implant. The equatorial region is between the anterior and posterior. Ruptures, specifically cracks, are formed predominantly in the equatorial region where the curvature is at its maximum (Schubert, 2013).

In a preferred embodiment, the fibers are oriented. This means that the fibers are not laid in random orientation, but aligned in a direction. Preferably, the fibers are aligned essentially in parallel. For example, electrospun fibers can be oriented by charging the support on which the fibers are spun, such that it determines the deposition direction of the spun or emerging fibers. Fibers are preferably oriented such that they stabilize weak regions of the implant and increase the resilience of the implant. Preferably, the oriented fibers stabilize tangential regions of the implant. Preferably, at least a portion of the oriented fibers cross the equatorial region and/or equatorial plane. More preferably, the fibers are oriented perpendicular to the equatorial region and/or equatorial plane. The amount of fibers is selected to achieve stabilization of the regions of the implant on which the fibers are deposited. Methods for aligning fibers by electrospinning are known in the art. A fiber reinforced silicone with aligned fibers, which is applicable according to the present invention, is disclosed in Bayley, 2011.

In a preferred embodiment, the surface of the fiber reinforced silicone and thus of the outer shell of the implant is textured (patterned). The texture is preferably a microstructure. It is known in the art that microstructures on the surface confer advantageous properties to breast implants. Microstructures can improve cell attachment, cellular behaviour and formation of new tissues. Moreover, microtextured surfaces can confer stability to the implants by reducing the risk of rupture (Schubert et al., 2013; see FIG. 9 thereof). The average lateral distance between indentations on the surface could be in the micrometer range.

In a highly preferred embodiment, the surface is textured by imprinting a pattern with crystals. Preferably, the crystals are water soluble, such as salts, preferably NaCl, or sugar (preferably household sugar). Preferably, the crystals are a sieving fraction having a defined size range. The pattern is typically imprinted with crystals before complete curing the surface. According to the invention, it was found that very fine microstructures can be imprinted with crystals, which have been sieved to achieve a specific grain size and consequently a deliberate texture/microstructure of the shell. Defined size fractions are available by consecutive sieving operations using sieves of increasingly smaller mesh size. When proceeding accordingly, very fine and uniform microstructures are obtainable, which have a high compatibility with tissue and cells, surprisingly combined with a much higher mechanical stability, as indicated by high stress at break and elongation at break. Preferably, the crystal fraction is obtained by sieving with a sieve having a mesh size below 200 µm, such as 150 µm, 100 µm and/or 63 µm. With such fine and uniform microstructures, the resilience of the implant can be significantly improved.

Preferably, the surface roughness $R_z$ is below 150 µm, more preferably below 100 µm or below 50 µm. Preferably, the surface roughness $R_z$ is at least 10 µm or at least 20 µm. Preferably, it is in the range from 10 µm to 150 µm, more preferably from 20 µm to 100 µm. Preferably, $R_z$ is determined according to DIN ISO 4287. $R_z$ could be a mean value of 5, 10, 20 or 100 measurements. Such a surface roughness is available by modifying the implant surface with fractionated crystals, thereby improving the resilience of the implant significantly.

Preferably, the average lateral distance (median (dx)) between indentations on the surface is between 45 µm and 210 µm, more preferably between 45 µm and 95 µm. The average length of surface indentations can be determined graphically from microscopic images. For example, distances between indentations can be obtained from cross sectional samples of an implant. A baseline x is then defined parallel to the surface with a y coordinate perpendicular to the surface. The lowest positions in all indentations are marked on the x baseline. Distances dx between adjacent indentations on the x axis are calculated. A median value (median (dx)) is determined from a sufficiently high number of distances, such as 200 or 500. The depth of each indentation can be determined on the y axis compared to the highest position of the sample. Such microstructures are available when treating the surface with a sieved fraction of crystals of corresponding size as outlined above.

In a preferred embodiment, the surface of the fiber reinforced silicone is textured, wherein preferably the texture is obtained in a process comprising modifying the surface with fractionated crystals, and/or wherein the surface roughness $R_z$ is preferably in the range from 10 µm to 150 µm.

Alternatively, the pattern could be engraved on the surface, for example by a laser technique or imprinting with stamps or foams. However, it was found that the specific surface structure obtained by imprinting crystals as outlined above is especially advantageous for stabilizing the silicone.

In a preferred embodiment, the surface of the implant or outer shell is textured and comprises oriented fibers for stabilizing potential rupture sites as outlined above. When combining these modifications, an optimized stability and resilience can be adjusted.

In principle, the fiber reinforced silicone can be produced by any methods in which the fibers are embedded in the silicone matrix. Typically, the fibers are impregnated with liquid silicone, which is subsequently crosslinked. For example, a fiber mat can be immerged into a silicone bath. Alternatively, a fiber mat on a support can be coated with silicone. In both methods, layers of silicone-coated fibers form laminates. A conventional process for producing fiber reinforced silicones is described in Swart et al., 2010, the section "composite preparation" on pages 2144/2145 and in FIG. 2. Typically, the fiber reinforced silicone is produced with shaping means for adapting the shape to a breast. Typical shaping means are forms on which the silicone is coated or moulds.

In a preferred embodiment, the fiber enforced silicone is produced by dip coating and/or electrospinning. Dip coating refers to a process in which a workpiece is dipped into a liquid silicone, thereby impregnating the workpiece with a layer of silicone which is subsequently cured.

Subject of the invention is also a method for producing an implant or outer shell, comprising the steps of:
(a) providing a support and a solution of the comb polymer,
(b) spinning the solution to obtain fibers of the polymer, preferably by electrospinning,
(c) depositing fibers of the comb polymer on the support,
(d) impregnating the fibers with a liquid silicone,
(e) at least partially curing the product of step (d), thereby obtaining a fiber enforced silicone, and
(f) optionally repeating steps (a) to (e) at least once, whereby the fiber enforced silicone obtained in step (e) is used as the support.

The support provided in step (a) may comprise a silicone layer, which becomes a part of the outer shell and implant. Typically, the comb polymer is spun in step (b) from a solution in organic solvent. The impregnation step (d), possibly followed by partial curing (e), can be repeated several times to obtain a desired thickness. Typically, after impregnating the fibers with liquid silicone in step (d), the liquid silicone is at least partially cured. Partial curing (partial crosslinking) is advantageous, because the workpiece can be handled and the next layer can be applied without deformation of the silicone surface of the workpiece due to creeping or flowing of viscous silicone. Further, tackiness can be maintained which is advantageous for addition of a further layer and/or fibers. It is preferred to carry out a final curing step after all layers of the outer shell or implant have been applied in order to enhance adhesion of the layers to each other. In a specific embodiment, the impregnating in step (d) is carried out by dip-coating. In dip-coating, the workpiece is immersed into a liquid silicone bath.

In a preferred embodiment, the method comprises the steps of:
(a) providing a support and a solution of the comb polymer in an organic solvent,
(b) electrospinning the solution to obtain fibers of the polymer,
(c) depositing fibers of the comb polymer on the support,
(d) impregnating the fibers with a liquid silicone,
(e) at least partially curing the product of step (d), thereby obtaining a fiber enforced silicone, and
(f) repeating steps (a) to (e) at least once, whereby the fiber enforced silicone obtained in step (e) is used as the support.

In a preferred embodiment, the fibers are oriented in an electrospinning process by positioning an electrode in the support. Fiber orientation can be mediated by directional movement of the support, for example by rotation. In the methods described, it is preferred to carry out a step (g) after step (f), in which the surface is textured before final curing, preferably by imprinting with crystals.

In the method, it is preferred that the emerging fiber enforced silicone adopts the shape of the outer shell for a breast implant during steps (a) to (f). Preferably, the shape is conferred to the product by the support, on which it is prepared. In this embodiment, the support is shaped as an outer shell for a breast implant or a part thereof. Alternatively, or in addition, the outer shell shape can be imparted to the fiber enforced silicone in a final shaping step (g), for example by cutting. If the method is for producing an implant, the implant can be obtained in a further step by combining the outer shell with a core.

Figure 1:
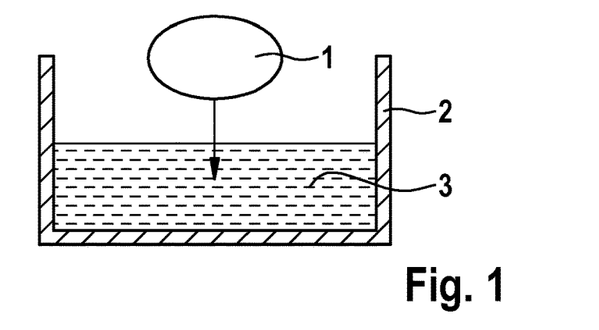
FIGS. 1 to 4 show schematically and in exemplified form how a support can be coated with silicone in a method of the invention.
Figure 2:
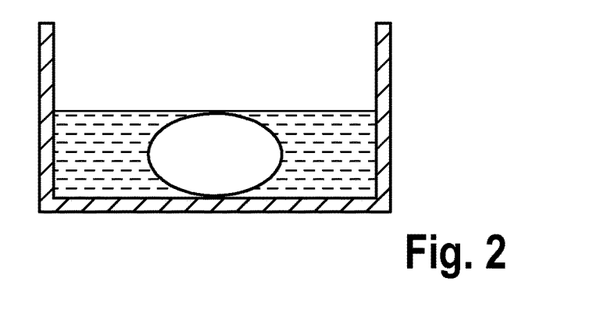
Figure 3:
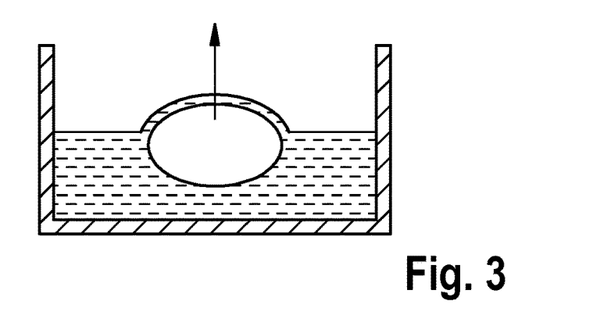
Figure 4:
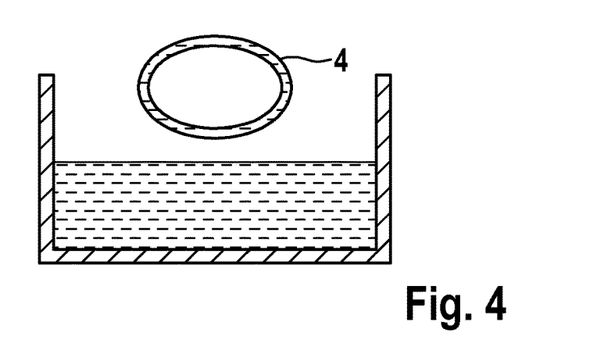

An exemplified and generalized method of the invention is demonstrated in FIGS. 1 to 7. FIGS. 1 to 4 show a dip coating process for depositing layers of silicone on a support or emerging workpiece. FIG. 1 shows a support 1, which is immerged into a container 2 comprising a silicone bath 3. The liquid silicone is uncured. The support has a form corresponding to the desired shape and size of the implant. The support could also be a workpiece, i.e. a form on which an intermediate product has already been produced. As shown in FIG. 2, the support can be fully immersed into the bath. As shown in FIGS. 3 and 4, the support is removed from the bath and a silicone coating 4 remains on the surface of the support. The coated support is partially cured to stabilize the structure and form. Further, by tackiness can be maintained which is advantageous for addition of a further layer and/or fibers. By repeating the process of FIGS. 1 to 4, a coating is obtained having a desired thickness, typically between 0.2 and 3 mm. After each impregnating step, a pre-curing step is preferably carried out. Pre-curing may be carried out by increasing the temperature, for example to 120° C. For common silicones, it can be roughly assumed that the curing temperature is correlated to the curing time, such that a temperature decrease of about 10° C. yields corresponds to an increase of the curing and pre-curing time by factor 2. Additional layers of silicone derivatives can be applied to the workpiece, for example a barrier layer, preferably a fluorinated silicone. Other silicone types may also be used for the barrier layer, but the diffusion constant through the barrier material should be at least less than 25% compared to the standard silicone.

Figure 5:
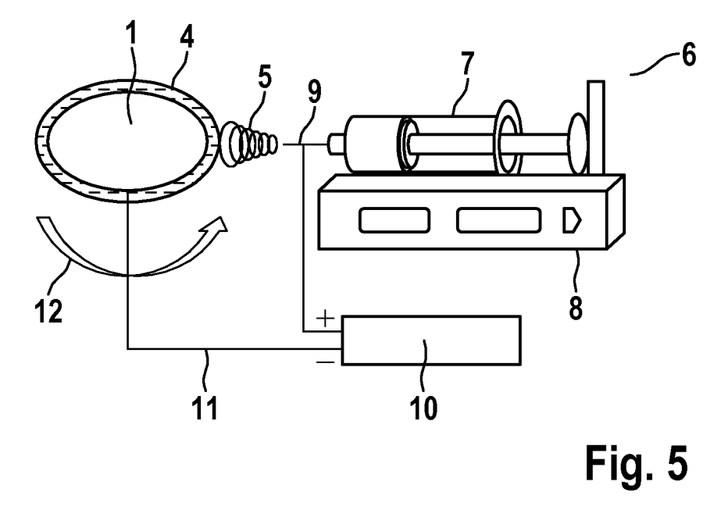
FIG. 5 shows schematically and in exemplified form an electro-spinning device for depositing fibers on a coated support.
Figure 6:
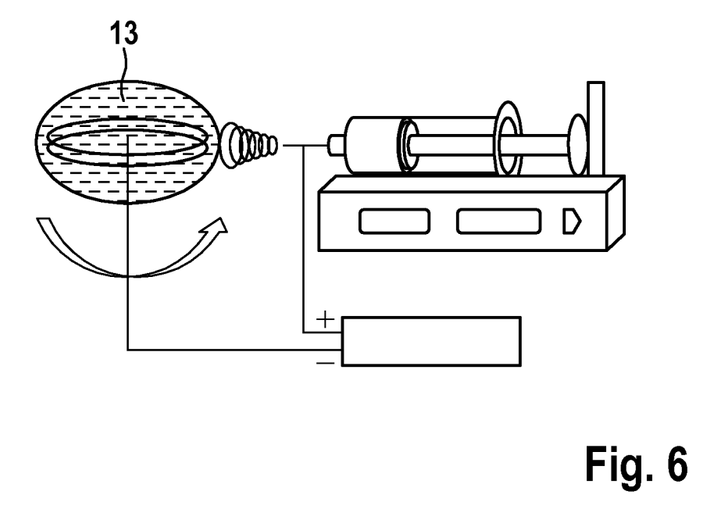
FIG. 6 shows schematically and in exemplified form a device of FIG. 5, in which a circular electrode is positioned in the support.
Figure 7A:
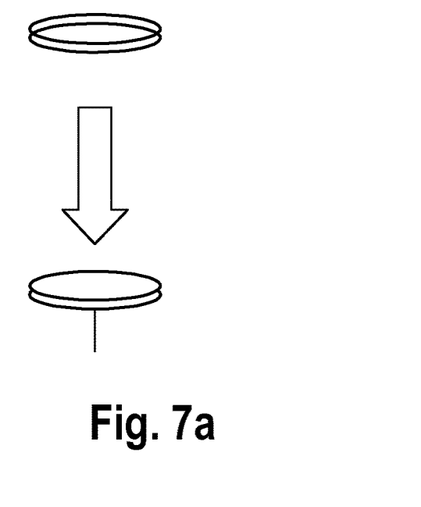
FIGS. 7a and 7b show schematically and in exemplified form designs of circular electrodes in the support.
Figure 7B:
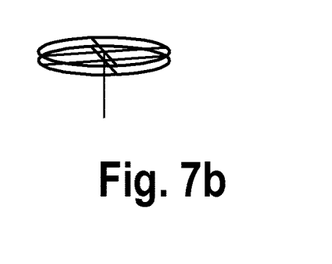

FIGS. 5 to 7 show an electro-spinning process for depositing fibers on the support or workpiece. Specifically, a coated support obtained in a dip coating process according to FIGS. 1 to 4 is used for application of fibers. FIG. 5 shows an electro-spinning device 6 comprising a pump 8 and syringe 7 for application of the fiber precursor, typically a solution of the comb polymer in organic solvent. The needle 9 of the syringe is an electrode and the other electrode can be under or in the support 1. Both electrodes are connected to a voltage source 10 by connection 11, which induces an electric field between needle 9 and support 1, thereby mediating formation of fibers 5 and deposition on the surface of support 1. The support can be moved, for example rotated, along direction 12, for achieving a uniform fiber distribution on the surface at least along the equatorial region of the implant. The support can be conductive and connected to the electrospinning device. FIG. 6 shows an internal view of the support with a double ring type collector electrode 13. This electrode type support provides uniform deposition of the fibers and orientation of the fibers, preferably in the equatorial region of the implant. FIG. 7 shows embodiments of circular electrodes for obtaining fiber orientation as parallel disks (FIG. 7a) or rings with connections to the center electrode contact (FIG. 7b).

A subsequent pre-curing step should then be applied to ensure sufficient fixation of the fibers on the under-laying system and to avoid movement of the fibers in the following processing steps. The coating and spinning process of FIGS. 1 to 7 can be repeated to obtain an outer shell and implant with multiple fiber layers embedded in a silicone matrix. The amount and direction of fibers in each layer can be adjusted to the desired strength and structure of the overall implant.

The process can be terminated with a final curing step. Before final curing, the outer shell or implant surface can be structured, for example with salt crystals. Addition of a final silicone layer according the above describe technique (FIGS. 1 to 4) is a prerequisite for a final structuring step of the surface. The liquid silicone layer just brought on the fibers is procured and then covered with salt (NaCl) of a predetermined particle size, for example by trickling and/or rolling on a salt covered plate. This is followed by a final curing typically at 120° C. for typically several hours up to 20 h and subsequent washing off the soluble salt with water. The negative imprint of the salt crystals remains engraved on the surface. To manufacture the complete implant, standard techniques to fill the implants and placing and sealing with patches can be applied.

The electrospinning process or certain steps thereof can be controlled and/or executed electronically.

The production process may comprise rotation of the support in a silicone bath and fiber-spinning on the surface at the same time or sequentially. When proceeding accordingly, a uniform composite is obtainable and the overall process is less complicated.

The silicone matrix may comprise additional layers. For example, one of the layers could be followed by a diffusion inhibition layer, for example by deposition of $TiO_2$. It has been shown in the art that such a layer may inhibit diffusion of low molecular weight compounds in the matrix.

The silicone matrix may comprise typical silicone elastomer compounds, such as derivatized silicone, for example with phenyl or fluorine groups. Such silicone derivatives can reduce diffusion of low molecular weight components in the silicone matrix.

In a specific embodiment, only portions of the layers of a laminate are crosslinked to each other. For example, sections without crosslinking connection can be obtained when locally applying separation agents, or locally curing the emerging workpiece. Such a structure may inhibit growth of cracks within the implant.

Another subject of the invention is the use of a fiber reinforced silicone in or as the outer shell of a breast implant, or for preparing an implant or the outer shell of a breast implant, wherein the fiber reinforced silicone is defined as above. Preferably, the use is for stabilizing the breast implant and/or improving the resilience of the breast implant. Specifically, the use is for preventing damages, especially ruptures and cracks, of the implant. Subject of the invention is also the use of fibers for reinforcing an outer shell or silicone breast implant, wherein the fibers are defined as above.

Subject of the invention is also a fiber reinforced silicone as described above for use in surgery and/or in therapy. Preferably, the use is for breast reconstruction and/or breast augmentation, wherein the fiber reinforced silicone is defined as above. The fiber reinforced silicone is used as an implant or part of an implant.

Subject of the invention is also the use of a breast implant or of an outer shell of a breast implant of the invention in surgery and/or in therapy, preferably for breast reconstruction and/or breast augmentation.

The breast implant and outer shell, methods and uses solve the above defined problem. A breast implant is provided which has a high stability and resistance to damages, especially cracks and ruptures. The likelihood of damages can be significantly decreased when known silicone materials are reinforced with comb polymer fibers. As demonstrated by the correlation between Weibull modulus and normalized strength $\sigma_0$ of the implant, the overall risk of ruptures is low. The structure and stability can be adapted to the specific requirements of breast implants. Moreover, silicone implants can be specifically and locally reinforced at desired positions, especially at sites prone to ruptures. Stabilization can also be achieved by orienting the fibers. The fibers have a good compatibility with and adhesion to the silicone matrix. The materials also have a good biocompatibility and high safety as required for breast implants. In view of the good stability, biocompatibility and safety and, the long-term stability can be expected to be high.

Exemplified embodiments of the invention and aspects of the invention are shown in the figures.

BRIEF DESCRIPTION OF THE DRAWINGS

FIG. 7a shows an embodiment of circular electrodes for obtaining fiber orientation as parallel disks. FIG. 7b shows an embodiment of circular electrodes for obtaining fiber orientation as rings with connections to the center electrode contact.

EXAMPLES

1. Preparation of Salt for Texturing

For later texturing, six particle size fractions were isolated from the commercial kitchen salt (trademark Zals, Eurovera Ltd. & KG). The salt was fractionated by consecutive sieving operations using 5 tests sieves with an aperture size of 500, 250, 150, 100 and 63 μm on an As200 test sieve shaker (Retsch GmbH). The sieves fulfil ISO 3310 and ASTM E11 (according to Retsch GmbH, 2015). Three ceramic balls were added to each sieve and the salt was treated at an amplitude of 2.5 mm for 8 min. Thereby, crystal fractions were obtained comprising crystals of about <63 μm (up to >0 μm), >63 μm (up to 100 μm), >100 μm (up to 150 μm), >150 μm (up to 250 μm) and >250 μm (up to 500 μm) and >500 μm.

2. Creating of a Curable Liquid Silicone Rubber (LSR) Blend for Mould Filling

The liquid silicone rubber (trademark Elastosil LR 3003/30, available from Wacker Chemie AG, DE) has a high tear strength and exceeds the required 450% minimum strain at break for mammary implants according to ISO 14607:2009. Additionally it has the same Shore Hardness (Type A) and a similar tear strength as addition cured silicone dispersion available under the trademark MED-6400 of NuSil Technology LLC, US, used for manufacturing of mammary implant shells by the former company Poly Implant Prothèse. Components A and B of Elastosil LR 3003/30 were weighted in ratio 1:1 and mixed at 1000 rpm for 5 min by a SAC 150 SP speed mixer (Hauschild & Co. KG). The ratio of 1:1 was kept with a resolution of 1 mass %.

3. Removing Dispersed Air for Better Mechanical and Surface Properties

The curable LSR blend is exposed to an under pressure of 0.4 mbar in a desiccator for 20 min. This was followed by mixing the blend for another 5 min at 1000 rpm and evacuating for 15 min at 0.4 mbar. Air removal is important, because otherwise the mechanical values such as $\sigma_0$ and m can be decreased.

4. Mould Filling and Preparation of a Homogeneous LSR Surface for Texturing

LSR specimen for texturing can be produced similar to commercial breast implants using the dip coating process. At a withdrawal speed of e.g. 2.5 mm/s a layer thickness of 1.81+/−0.30 mm was achieved. Other thicknesses can be manufactured by adapting the viscosity and/or the withdrawal speed. The desired thickness should be manufactured under adaption of the withdrawal speed if the desired recipe remains unmodified. The thickness can be adjusted according to the equation (thickness~viscosity$^n$ velocity$^m$), wherein n and m are in the range between 0.5 and 0.7 (mostly 0.5) and in most cases n=m. For achieving a greater volume, LSR test stripes of a thickness of 0.50 mm; 0.75 mm and 1.00 mm were made by casting the curable blend into a milled PTFE trough mould. The casting was fastened by spreading the LSR with a doctor blade. At first the material was spread in greater thickness than the final stripe. Then dispersed air is drawn to the surface through under pressure of 0.4 mbar for 15 min. In a second step the bubble containing surplus of LSR at the surface was removed with a doctor blade. Thereby the withdrawal speed of the doctor blade was 5+/−2.5 mm/s. If 10 min at 0.4 mbar caused yet again air bubbles at the surface, more LSR was added and the casting procedure was repeated.

5. Preparation of Composite

For preparation of a composite, electrospun fibers from poly(methyl methacrylate)-graft-poly(dimethyl siloxane) copolymer (PMMA-g-PDMS) were used which had been prepared according to the process described in Swart et al., 2010 (see section experimental, copolymer synthesis and electrospinning procedure). A silicone composite was prepared in line with Swart et al, 2010 (experimental, composite preparation) with an LSR blend as in examples 2 to 4 above. In brief, a thin layer of the uncured LSR was evenly spread on a piece of non-stick Teflon® surface. This layer was subjected to vacuum to remove any air bubbles remaining from the mixing of silicone oligomers with catalyst. A pre-cut piece of nanofiber mat was gently placed on top of the silicone layer and completely wetted. The system was repeatedly placed under vacuum to remove air. Additional silicone was placed on top of the fiber mat to ensure complete coverage of the fibers and uniform wetting. The system was placed in an air ventilated oven and allowed to cure for 20 h at 120° C.

6. Texturing

Figure 10:
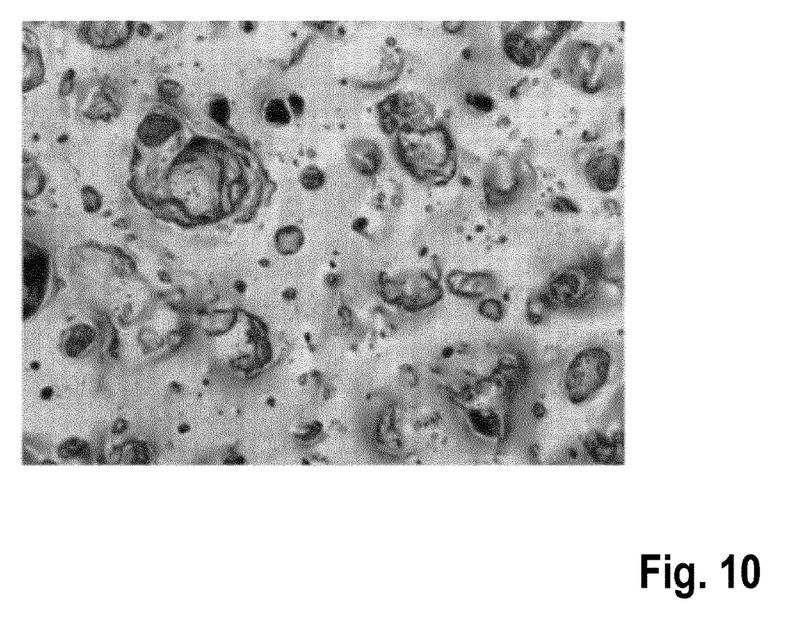
FIG. 10 shows a textured surface of a silicone implant obtained with fractionated crystals having a size below 63 μm according to example 6.

The surfaces of homogeneous LSR prepared according to the examples above were textured with salt crystal fractions obtained by sieving according to example 1. From a height of 4+/−3 cm, a salt fraction prepared was trickled on the prepared surface and then distributed by tilting and shaking. Particle impact and weight as well as surface tension and deformation were responsible for the degree of particle sinking in. For shells manufactured by dip coating the outer (last) layer is additionally brought in contact with salt or sugar or other soluble substances, preferably water soluble solid substances. Therefore it is possible in a subsequent step to wash out the above describe salt, sugar or other dissolvable substance to achieve a desired surface structure. The applied solvent should not dissolve or substantially swell the LSR material. The specimens were cured at typically 120° C. for up to 20 h. After cooling down to room temperature, the salt was removed by running tap water for 4 min. A textured surface obtained with fractionated crystals having a size below 63 µm is shown in FIG. 10. By this process, surface structures very similar to those of commercial silicone breast implants could be created at a comparable thickness. However, a fractionation of salt with respect to grain size enables deliberate textures.

7. Surface Roughness of Textured Products

The mean surface roughness $R_z$ was determined according to DIN ISO 4287 for a series of textured silicone products obtained according to the examples above without reinforcing fibers. To achieve comparable information about the dimensions of the surface texture generated, the surface roughness was investigated. According to DIN EN ISO 4287 the mean surface roughness $R_z$ was determined. Therefore images of the textured surface were taken with a 3D laser scanning microscope (Keyance VK-9700). For determination of the $R_z$ values, the sampling length and the filter parameters were selected according DIN EN ISO 4288 and DIN EN ISO 3274, respectively. The results with mean values and standard deviation of the six surface textures are summarized in table 1 below. The mean value and standard deviation was obtained from five measurements each. The results demonstrate that a large variety of $R_z$ values is accessible by texturing silicone implants with salt fractions according to the above described procedure.

TABLE 1

Mean surface roughness $R_z$ according to DIN ISO 4287 of six surfaces textured with salt fractions

| Texture [µm] | $R_z$ (µm) |
|---|---|
| >500 | 623.05 ± 57.02 |
| >250 | 508.74 ± 62.21 |
| >150 | 146.50 ± 4.19 |
| >100 | 172.45 ± 1.82 |
| >63 | 123.83 ± 5.51 |
| <63 | 24.80 ± 0.85 |

Further, the average lateral distance (medium (dx)) between indentations on the surface was determined graphically from microscopic images of cross sectional samples. A baseline x was defined parallel to the surface with a y coordinate perpendicular to the surface. The lowest positions in all indentations are marked on the x baseline. Distances dx between adjacent indentations on the x axis were calculated. The median (dx) was determined as 420.9 µm for the >500 µm sample, 283.9 µm for the >250 µm sample, 211.1 µm for the >150 µm sample, 149.4 µm for the >100 µm sample, 75.3 µm for the >63 µm sample and 47.7 µm for the <63 µm sample.

Figure 9:
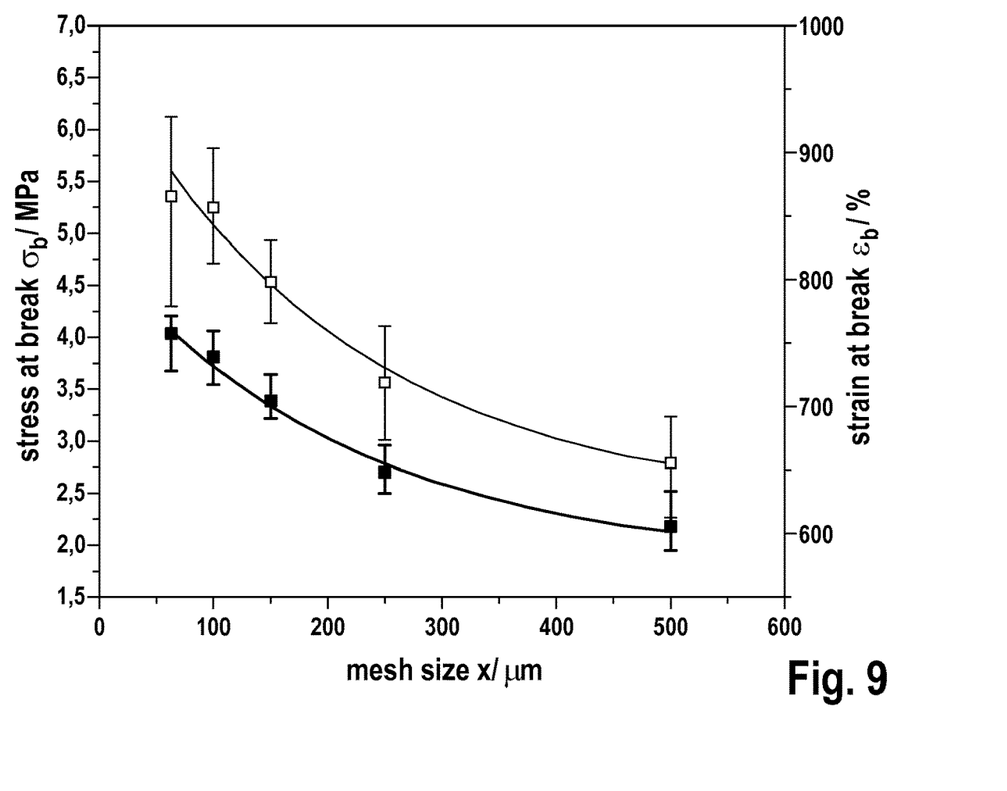
FIG. 9 shows the influence of mesh size on stress and strain at break as determined in example 9. One data point represents median and IQR from about 90 tensile specimen of a thickness between 0.50 mm and 1.00 mm, which is typical for commercial implants as shown in Daenicke, 2012. The open squares relate to strain at break and the black squares to stress at break.

8. Influencing Mechanical Properties by Varying Size of Salt Particles Used for Texturing The mechanical properties were determined by tensile testing. Three stripes textured with salt particles of each fraction were produced according to the examples above, but without incorporation of fibers. This was done for each of the thicknesses 0.50 mm, 0.75 mm and 1.00 mm. Ten dumbbell specimens shaped according to DIN 53504 type S3 were punched out of each stripe. They were tested in a Zwick/Roell Frank-811110™ universal testing machine according to DIN 53504, but with an elongation speed of 20 mm/min instead of 200 mm/min. As a measure for the size of the salt particles the mesh width is used in the following. The effect of varying the mesh size on stress at break and strain at break is shown in FIG. 9. By reducing the mesh size from 500 μm to 63 μm the median of stress at break could be increased by more than 85% from 2.17 MPa (IQR: 0.58 MPa) to 4.04 MPa (IQR: 0.52 MPa). The median of strain at break at the same time could be raise by over 30% from 656.56% (IQR: 81.96%) to 865.57% (IQR: 149.41%). Reducing the size of the salt particles by using sieves with smaller mesh size improves the stress at break and the strain at break simultaneously. Smaller particles cause smaller indentions on the surface and thereby cause lesser deterioration of the mechanical properties. In addition, it was found that thicker silicone layers while using the same particles for texturing increase the mechanical properties by increasing the portion of not deteriorated material (data not shown). Overall, the data demonstrates that fine microstructures provided with fine sieved crystals can significantly enhance the mechanical stability of silicone implants.

9. Resilience of the Products

Figure 8:
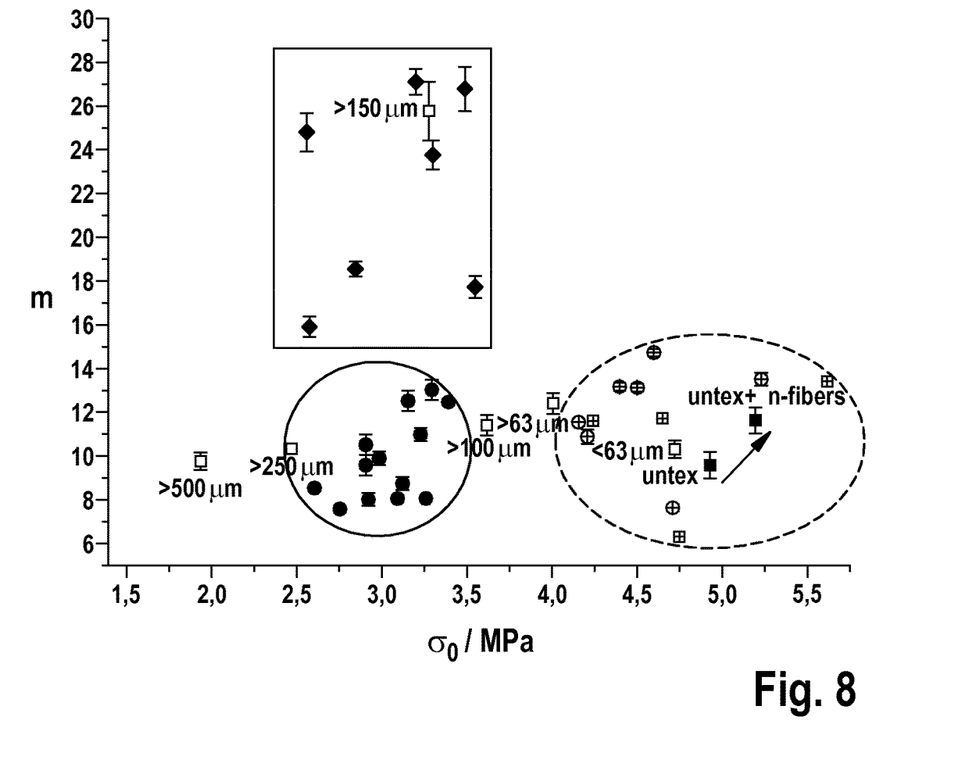
FIG. 8 shows in graphical form the correlation between Weibull modulus m and normalized strength $\sigma_0$ of various breast implants of the state of the art and an inventive implant. Where appropriate, the texture of the implant is specified in micrometers. The values are indicated for commercially available implants of Poly Implant Prothese (PIP) microtextured (white circles) and textured (black circles); a commercially available non-PIP standard implant (black rhombus), a series of textured silicone implants produced according to example without nanofibers with different average distances between indentations (white squares), and untextured silicone implants without and with nanofibers (black squares, the effect of nanofibers and increase of stability is demonstrated by the arrow).

The resilience of products obtained as described above was examined by determining parameters $\sigma_0$ and $m$ and graphical evaluation in a Weibull plot according to the method described in Schubert et al., 2013. The results and values for conventional silicone implants are summarized in FIG. 8. A series of textured silicone stripes without nanofibers was examined, wherein the average depths of indentations and average distances between indentations were decreased by applying smaller sized salt fractions from >500 μm to <63 μm according to example 6 above. The open squares in FIG. 8 indicate the general improvement of resilience by modifying the implant shell structure from rough to smaller microstructures to smooth. Further, silicone stripes were prepared according to the examples with and without nanofibers (FIG. 8, black squares). The shift along the arrow demonstrates the improvement by adding the fibers. Overall, the results show that by inclusion of fibers into the silicone matrix, the stability parameters can be shifted into a region which is highly advantageous for use of breast implants and long-term stability. A fine microstructure can impart additional stability to the implant.

LITERATURE

Bayley et al., "Large strain and toughness enhancement of poly(dimethyl siloxane) composite films filled with electrospun polyacrylonitril-graft-poly(dimethyl siloxane) fibers and multi-walled carbon nanotubes", 2011, Polymer 52, 4061-4072

Colas and Curtis, "Silicone biomaterials: history and chemistry & medical applications of silicones", 2005, from "An introduction to materials in medicine", Biomaterials Science, 2$^{nd}$ edition, editor: Ratner et al., Elsevier, Inc.

Daenicke, Jonas, "Kartierung and Untersuchung der mechanischen Eigenschaften von Silicon-Brustimplantathüllen", Bachelor Thesis, 2012, Friedrich-Alexander-Universität Erlangen Nürnberg Daniels, "Silicone breast implant materials", 2012, Swiss Medical Weekly, 142:w13614

RETSCH GMBH, Sieve Analysis—Taking a Close Look at Quality—An Expert Guide to Particle Size Analysis, 2015, http://www.retsch.com/dltmp/www/53e4b562-5294-4711-9111-636500000000-c5e17882ae92/expert_guide_sieving_en.pdf, Accessed 23 Sep. 2015

Schubert et al., "On the failure of silicone breast implants: new insights by mapping the mechanical properties of implant shells", 2013, Polymer International, DOI 10.1002/pi.4619

Swart et al., "Organic-inorganic hybrid copolymer fibers and their use in silicone laminate composites", 2010, Polymer Engineering and Science, DOI 10.1002/pen

LIST OF REFERENCE SIGNS

1 support
2 container
3 silicone bath
4 silicone coating
5 fibers
6 electrospinning device
7 syringe
8 pump
9 needle
10 voltage source
11 connection
12 direction
13 double ring type collector electrode

The invention claimed is:

1. An outer shell of a breast implant, wherein the outer shell comprises a fiber reinforced silicone comprising
   (A) a silicone matrix and
   (B) fibers embedded in the silicone matrix,
wherein the fibers comprise a comb polymer having a base polymer and side chains, wherein the base polymer is an organic polymer and the side chains comprise polysiloxanes.

2. The outer shell of a breast implant according to claim 1, wherein the polysiloxane side chains are linked to the base polymer via ester bonds, amide bonds or ether bonds.

3. The outer shell of a breast implant according to claim 1, wherein the comb polymer comprises
   a) at least one structural unit A wherein
$R^1$ independently of one another represents H or $CH_3$;
$R^2$ independently of one another represents an ester group —CO—O—, an amide group —CO—NH—, an ether group —O— or no group (void),

R³ independently of one another represents —R⁷—Y—, wherein R⁷ is a $C_1$-$C_6$ alkylene group, and Y is either no group (void) or O, R⁴ independently of one another represents $C_1$-$C_4$ alkyl, R⁵ independently of one another represents $C_1$-$C_{18}$ alkyl, n independently of one another is a value between 5 and 2000, and b) at least one structural unit B wherein R¹ independently of one another represents H or $CH_3$;

R² independently of one another represents H or $CH_3$,

R³ independently of one another represents H or $CH_3$,

R⁴ independently of one another represents H, —CN, —COO—R⁶, —O—R⁶, —CO—N—R⁶ or —R⁶, wherein R⁶ is $C_1$-$C_8$ alkyl.

4. The outer shell of a breast implant according to claim 1, wherein the fibers are electrospun.

5. The outer shell of a breast implant according to claim 1, wherein the fibers are oriented.

6. The outer shell of a breast implant according to claim 5, wherein at least a portion of the oriented fibers cross the equatorial region and/or equatorial plane of the implant.

7. The outer shell of a breast implant according to claim 1, wherein the surface of the fiber reinforced silicone is textured.

8. The outer shell of a breast implant according to claim 1, wherein the fiber reinforced silicone is a laminate comprising at least two layers of fibers.

9. A breast implant comprising an outer shell of claim 1 and a core.

10. A method for producing an outer shell of claim 1, wherein production of the fiber reinforced silicone comprises dip coating and/or electrospinning.

11. A method for producing an outer shell of claim 1, comprising the steps of:
(a) providing a support and a solution of the comb polymer,
(b) spinning the solution to obtain fibers of the polymer,
(c) depositing fibers of the comb polymer on the support,
(d) impregnating the fibers with a liquid silicone,
(e) curing the product of step (d), thereby obtaining a fiber reinforced silicone, and
(f) optionally repeating steps (a) to (e) at least once, whereby the fiber reinforced silicone obtained in step (e) is used as the support.

12. The method of claim 10, wherein the fibers are oriented by electrospinning by an electrode in the support.

13. A method for producing a breast implant or the outer shell of a breast implant, which comprises including in a breast implant or an outer shell of a breast implant a fiber reinforced silicone, wherein the fiber reinforced silicone comprises
(A) a silicone matrix and
(B) fibers embedded in the silicone matrix,
wherein the fibers comprise a comb polymer having a base polymer and side chains, wherein the base polymer is an organic polymer and the side chains comprise polysiloxane.

14. A method which comprises implanting a breast implant in a female human, wherein the breast implant comprises a fiber reinforced silicone, wherein the fiber reinforced silicone comprises
(A) a silicone matrix and
(B) fibers embedded in the silicone matrix,
wherein the fibers comprise a comb polymer having a base polymer and side chains, wherein the base polymer is an organic polymer and the side chains comprise polysiloxane.

15. A method which comprises implanting a breast implant in a human female, wherein the breast implant comprises an outer shell of claim 1.

16. The outer shell of a breast implant according to claim 3, wherein:
in the at least one structural unit A,
R⁷ is methylene, ethylene or propylene,
R⁴ independently of one another represents methyl or ethyl,
R⁵ independently of one another represents $C_1$-$C_6$ alkyl,
n independently of one another is a value between 20 and 1000, and
in the at least one structural unit B,
R² represents H,
R³ represents H,
R⁶ is methyl or ethyl.

17. The outer shell of a breast implant according to claim 7, wherein the texture is obtained in a process comprising modifying the surface with fractionated crystals, and/or
wherein the surface roughness $R_Z$ is in the range from 10 μm to 150 μm, and/or
wherein the average lateral distance (median (dx)) between indentations on the surface is between 45 μm and 210 μm.

18. A method for producing an outer shell of claim 11, which comprises
in step (b), spinning the solution to obtain fibers of the polymer by electrospinning, and
in step (d), impregnating the fibers with a liquid silicone by dip coating.

19. The method of claim 14, wherein the method comprises breast reconstruction and/or breast augmentation.

20. The method of claim 15, wherein the method comprises breast reconstruction and/or breast augmentation.

* * * * *